United States Patent
Hanson et al.

(10) Patent No.: US 6,433,198 B1
(45) Date of Patent: Aug. 13, 2002

(54) PREPARATION OF 6-α-HYDROXY-7-DEOXYTAXANES USING NOCARDIOIDES LUTEUS OR A HYDROXYLASE ISOLATED THEREFROM

(75) Inventors: Ronald L. Hanson, Morris Plains; Ramesh N. Patel, Bridgewater, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 2 days.

(21) Appl. No.: 09/615,436

(22) Filed: Jul. 13, 2000

Related U.S. Application Data

(62) Division of application No. 09/231,702, filed on Jan. 14, 1999.
(60) Provisional application No. 60/071,331, filed on Jan. 14, 1998.
(51) Int. Cl.$^7$ .............................................. C07D 493/00
(52) U.S. Cl. ...................................... 549/510; 549/511
(58) Field of Search ................................. 549/510, 511

(56) References Cited

U.S. PATENT DOCUMENTS

| | | | | |
|---|---|---|---|---|
| 5,478,854 A | | 12/1995 | Farina et al. ................ | 514/374 |
| 5,516,676 A | * | 5/1996 | Hanson ....................... | 435/123 |
| 5,523,219 A | * | 6/1996 | Hanson ....................... | 435/123 |
| 5,739,016 A | * | 4/1998 | Hanson ....................... | 435/123 |

OTHER PUBLICATIONS

Kumar et al., Cancer Chemother Pharmacol, vol. 36, pp. 129–135 (1995).

* cited by examiner

Primary Examiner—Amelia Owens
(74) Attorney, Agent, or Firm—Kenneth W. Peist

(57) ABSTRACT

An enzymatic hydroxylation method for the preparation of compounds useful as intermediates in the preparation of taxanes such as 6-α-hydroxy-7-deoxypaclitaxel, wherein one or more C-6 hydrogen-bearing taxanes are contacted with an enzyme or microorganism capable of hydroxylating said C-6 carbon to give C-6 hydroxyl-bearing taxane.

8 Claims, No Drawings

PREPARATION OF 6-α-HYDROXY-7-DEOXYTAXANES USING NOCARDIOIDES LUTEUS OR A HYDROXYLASE ISOLATED THEREFROM

This application is a Divisional of Ser. No. 9/231,702 filed Jan. 14, 1999 and claims priority benefit of Provisional Application No. 60/071,331 filed Jan. 14, 1998.

FIELD OF THE INVENTION

The present invention is directed to an enzymatic hydroxylation method for the preparation of 6-α-hydroxy-7-deoxytaxanes, useful as intermediates in the preparation of taxanes, and particularly in the preparation of paclitaxel, paclitaxel analogues, and second and third generation paclitaxel-like compounds.

BACKGROUND OF THE INVENTION

Taxanes are diterpene compounds which find utility in the pharmaceutical field. For example, paclitaxel (Taxol®), a taxane having the structure:

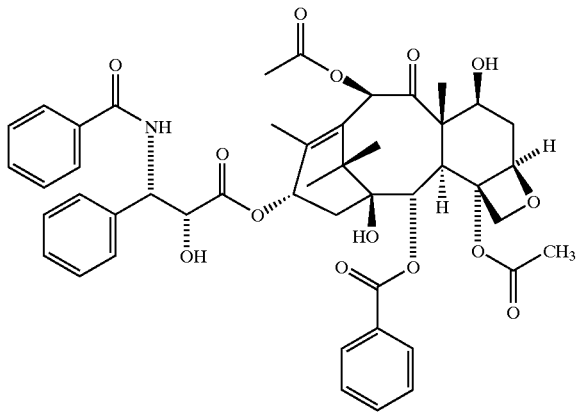

has been found to be an effective anticancer agent.

Naturally occurring taxanes such as paclitaxel, 10-deacetylpaclitaxel and baccatin III can be extracted with some difficulty from the trunk bark of different species of Taxus (yew). Paclitaxel, in particular, may be extracted from the inner bark of *Taxus brecifolia*. Although *T. brevifolia* is a relatively common tree in the Pacific Northwest, it is a slow growing plant and is indigenous to the ecologically threatened old-growth forests of this area, and harvesting is thus increasingly restricted because of environmental concerns.

As yields of paclitaxel extracted from *T. brevifolia* are generally low, of the order of 100 mg/kg, semisynthetic methods of producing paclitaxel from baccatin III and 10-deacetylbaccatin have proven successful and are routinely practiced. Baccatin III, 10-deacetylbaccatin, as well as other paclitaxel precursors may be isolated from the needles of the European yew, *Taxus baccata* in relatively larger quantities, e.g. approximately 300 mg/kg of 10-deacetylbaccatin may be obtained from yew leaves. Although yew needles generally provide an adequate supply of the necessary starting materials for synthesizing paclitaxel, the supply is not endless and other methods of easing the supply dilemma and producing adequate amounts of paclitaxel have become a priority. The art has thus continued to search for synthetic, including semisynthetic routes for the preparation of naturally occurring taxanes such as paclitaxel, as well as the preparation of paclitaxel analogues and second and third generation paclitaxel-like compounds thereof.

Recently, endophytic microbes associated with *T. brevifolia* were examined as potential alternative sources of paclitaxel. Stierle et al., in "Bioactive Metabolites of the Endophytic Fungi of Pacific Yew, *Taxus brevifolia*", ACS 1995, have confirmed that the fungus *Taxomyces andreanae*, isolated from the inner bark of a yew tree in Montana, has demonstrated the ability to produce paclitaxel.

Paclitaxel is converted to 6-α-hydroxy paclitaxel in human liver by cyp2C8, and loses most of its cytotoxicity as a result of this hydroxylation Such activity is evidenced by studies performed by Kumar et al, "Comparative in vitro Cytotoxic Effects of Paclitaxel and Its Major Human Metabolite 6α-hydroxypaclitaxel", *Cancer Chemother. Pharmacol.* 36: 129–135 (1995), and by Rahman et al., "Selective Biotransformation of Paclitaxel to 6-α-hydroxypaclitaxel by Human Cytochrome P450 2C8", *Cancer Research,* 54: 5543–5546 (1994). To avoid this problem, second generation analogs are being developed. Compounds such as 6-α-hydroxy-7-deoxytaxanes or compounds derived therefrom may be useful as second generation drugs. The chemical preparation of these compounds requires a long sequence of reactions to incorporate oxygen at C6. An enzyme able to hydroxylate the 6-position of a 7-deoxytaxane would afford a much simpler route. Although human cyp2C8 converts paclitaxel to 6-α-hydroxypaclitaxel, it has not been shown to be effective with 7-deoxypaclitaxel or 7-deoxybaccatin. We have, therefore, derived another enzyme source for this transformation.

SUMMARY OF THE INVENTION

The present invention provides for a process of preparing 6-α-hydroxy-7-deoxytaxanes using microorganisms or enzymes derived therefrom for hydroxylation of 7-deoxytaxanes at C-6 to give 6-α-hydroxy-7-deoxytaxanes from which taxanes having a desired sidechain at C-13 or containing another modification, may subsequently be synthesized.

In particular, the present invention provides a method for the preparation of at least one taxane having a hydroxyl group directly bonded at C-6, comprising the steps of contacting at least one taxane having a deoxygenated C-7 with an enzyme or microorganism capable of effecting said hydroxylation at C-6.

DETAILED DESCRIPTION OF THE INVENTION

The present invention provides an efficient method for the preparation of 6-α-hydroxy-7-deoxytaxanes from 7-deoxytaxanes. The present invention is described further as follows.

In a preferred embodiment, the present invention provides a method for the preparation of at least one 6-α-hydroxy-7-deoxytaxane of the following formula I:

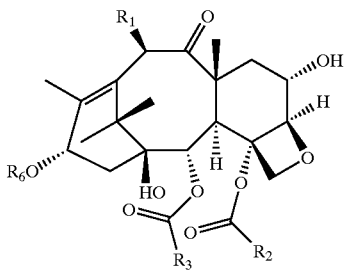

(I)

where
R$_1$ is hydrogen, hydroxyl, R$_4$—O—, or R$_5$—C(O)—O—;
R$_2$ and R$_3$ are independently hydrogen, alkyl, alkenyl, alkynyl, cycloalkyl, cycloalkenyl, aryl, or heterocyclo;
R$_4$ is a hydroxyl protecting group;
R$_5$ is a hydrogen, alkyl, alkenyl, alkynyl, cyclocalkyl, cycloalkenyl, aryl or heterocyclo; and
R$_6$ is hydrogen, a hydroxyl protecting group such as triethylsilyl, or an acyl group such as a paclitaxel side chain, cephalomannine side chain, or taxol analog side chain;
or salts, thereof, comprising the steps of contacting at least one 7-deoxytaxane of the following formula II:

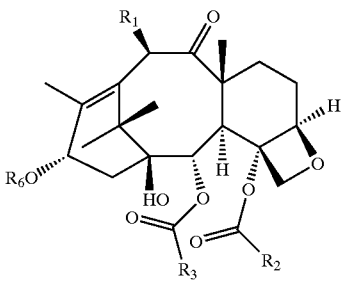

(III)

where R$_1$, R$_2$, R$_3$ and R$_6$ are as defined above,
or salts thereof, with an enzyme or microorganism capable of effecting the hydroxylation at C-6 on said taxane. All stereoconfigurations of the unspecified chiral centers of the compounds of the formulae I and II are contemplated in the method of the present invention, either alone (that is, substantially free of other stereoisomers) or in admixture with other stereoisomeric forms. Furthermore, this method may also be utilized in the preparation of the 6-β-hydroxy-deoxytaxane isomer.

In another embodiment, the present invention provides a method for the preparation of at least one first taxane, having a desired 6-α-hydroxy-7-deoxytaxane, from at least one second taxane having a C-10 acetyl, and having no hydroxyl group directly bonded at C-7, by enzymatic hydrolysis of the C-10 acetyl to provide at least one 10-deacetyl-6,7-dideoxy analogue by the method described herein, followed by attachment of the desired hydroxyl group at C-6 to provide the former. In this embodiment, the present invention provides, for example, a method for the preparation of a desired taxane having a hydroxyl group directly bonded at C-6, from a starting material of 7-deoxy-10-acetyltaxane by simultaneous or sequential hydrolysis of the 7-deoxy-10-acetyltaxane to provide a C-10 deacetyltaxane, followed by the coupling of the desired hydroxyl group at C-6. The 6-α-hydroxy-7-deoxytaxane product of the enzymatic process of the present invention includes a hydroxyl group directly bonded at C-13 and which may undergo later subsequent reaction as part of the semisynthesis of paclitaxel from the 7-deoxytaxane starting material.

The terms "enzymatic process" or "enzymatic method", as used herein, denote a process or method of the present invention employing an enzyme or microorganism. The term "hydroxylation", as used herein, denotes the formation of a hydroxyl group, and may be achieved, for example, by contact with oxygen and a suitable reductant according to the method of the present invention. Use of "an enzyme or microorganism" in the present method includes use of a single, as well as two or more, enzymes or microorganisms.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH) alkyloxycarbonyl, alkylcarbonyloxy, carbamoyl (NH$_2$—CO—), amino (—NH$_2$), mono- or dialkylamino or thiol (—SH).

The terms "lower alk" or "lower alkyl", as used herein alone or as part of another group, denote such optionally substituted groups as described above for alkyl having 1 to 4 carbon atoms in the normal chain.

The terms "alkoxy" or "alkylthio", as used herein alone or as part of another group, denote an alkyl group as described above bonded through an oxygen linkage (—O—), or a sulfur linkage (—S—), respectively. The term "alkyloxycarbonyl", as used herein alone or as part of another group, denotes an alkoxy group bonded through a carbonyl group. The term "alkylcarbonyloxy", as used herein alone or as part of another group, denotes an alkyl group bonded through a carbonyl group which is, in turn bonded through an oxygen linkage. The terms "monoalkylamino" or "dialkylamino", as used herein alone or as part of another group, denote an amino group substituted by one or two alkyl groups as described above, respectively.

The term "alkenyl", as used herein alone or as part of another group, denotes such optionally substituted groups as described above for alkyl, further containing at least one carbon to carbon double bond. Exemplary substituents include one or more groups described above as alkyl substituents. The term "alkenyloxy", as used herein alone or as part of another group, denotes an alkynyl, group as described above bonded through an oxygen linkage (—O—).

The term "cycloalkyl", as used herein alone or as part of another group, denotes optionally substituted, saturated carbocyclic ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents. The term "cycloalkyloxy", as used herein alone or as part of another group, denotes a cycloalkyl group as described above bonded though an oxygen linkage (—O—).

The term "cycloalkenyl", as used herein or as part of another group, denotes such optionally substituted groups as described above for cycloalkyl, further containing at least one carbon to carbon double bond forming a partially unsaturated ring. Exemplary substituents include one or more alkyl groups as described above as alkyl substituents. The term "cycloalkenyloxy", as used herein alone or as part of another group, denotes a cycloalkenyl group as described above bonded though an oxygen linkage (—O—).

The term "ar" or "aryl", as used herein alone or as part of another group, denote optionally substituted, carbocyclic aromatic groups, preferably containing 1 or 2 rings and 6 to 12 ring carbons. Exemplary unsubstituted such groups include phenyl, biphenyl, and napthyl. Exemplary substituents include one or more, preferably three or fewer, nitro groups, alkyl groups as described above and/or groups described as alkyl substituents. The term "aryloxy", as used herein alone or as part of another group, denotes an aryl group as described above bonded through an oxygen linkage (—O—).

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, and benzofurazanyl. Exemplary substituents include one or more alkyl groups as described above and/or one or more groups described above as alkyl substituents. The term "heterocyclooxy", as used herein alone or as part of another group, denotes a heterocyclo group as described above bonded through an oxygen linkage (—O—).

The terms "halogen" or "halo", as used herein alone or as part of another group, denote chlorine, bromine, fluorine and iodine.

The term "taxane", as used herein, denotes compounds having a taxane moiety as described following. The term "taxane moiety", as used herein, denotes moieties containing the core structure (with numbering of ring system positions used herein shown):

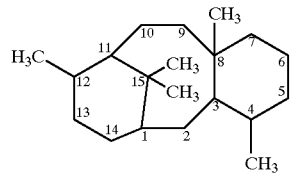

which core structure may be substituted and which may contain ethylenic unsaturation in the ring system thereof. Such moieties have an oxetane ring fused at the 4- and 5-positions, such as is found in paclitaxel, are preferred.

The term "hydroxy (or hydroxyl) protecting group", as used herein, denotes any group capable of protecting a free hydroxyl group which, subsequent to the reaction for which it is employed, may be removed without disturbing the remainder of the molecule. Such groups, and the synthesis thereof, may be found in "Protective Groups in Organic Synthesis" by T. W. Greene, John Wiley and Sons, 1981, or Feiser & Feiser.

The term "salt", as used herein, includes acidic and/or basic salts formed with inorganic and/or organic acids and bases.

The term "acyl", as used herein alone or as part of another group, denotes the moiety formed by removal of the hydroxyl group from the group —COOH of an organic carboxylic acid. The term "acyloxy", as used herein alone or as part of another group, denotes an acyl group as described above bonded through an oxygen linkage (—O—).

Starting Materials

The 7-deoxytaxanes employed as starting materials for the present invention may be any such compounds capable of undergoing the enzymatic hydroxylation of the present invention. The starting materials may be synthetically formed taxanes, or preferably, naturally formed taxanes such as paclitaxel, 10-deacetylpaclitaxel, baccatin III, 7-deoxybaccatin III, 7-deoxy-10-deacetylbaccatin III, alone or in admixture with each other. The "naturally formed" taxane starting materials are preferably obtained by plant cell culture of, and/or extraction from, taxane-producing plant tissues, particularly tissues from, or derived from plants of the Taxus genus such as *Taxus baccata, Taxus cuspidata, taxus brevifolia, Taxus wallichiana, Taxus media, Taxus hicksii,* especially Taxus x. media *hicksii.* Exemplary plant tissues include the needles, bark and whole seedlings.

Preferred methods of obtaining the 7-deoxytaxane starting materials of the present invention have been reported such as by Farina et al. in U.S. Pat. No. 5,478,854; by Chaudhary et al. in *J. Org. Chem.,* 58, pp. 3798–3799 (1993); by Chen et al. in *J. Org. Chem.,* 58, pp. 5028–5029; and *Bioorganic & Medicinal Chemistry Letters,* 4, No. 18, pp. 2223–2228 (1994); the disclosures which are herein incorporated by reference herein; or according to the Examples herein.

Enzymes and Microorganisms

The enzyme or microorganism employed in the present invention may be any enzyme or microorganism capable of catalyzing the enzymatic hydrolysis described herein. The enzymatic or microbial materials, regardless of origin or purity may be employed in the free state or immobilized on a support such as by physical adsorption or entrapment.

Exemplary microorganisms, which have been identified through a random screening process, include those within the following genera: Nocardioides, Nocardia, Rhodococcus, Micropolyspora, Saccharopolyspora, Pseudonocardia, Oerskovia, Promicronospora, and Intrasporangium. Particularly preferred microorganisms are those species within the genus Nocardioides, such as *Nocardioides albus, Nocardioides luteus, Nocardioides simplex,* and *Nocardioides thermolilacinus,* especially *Nocardioides luteus* ATCC 55426 (SC13912). The term "ATCC" as used herein refers to the accession number of the American Type Culture Collection, 12301 Parklawn Drive, Rockville, Md., 20582, the depository for the organism referred to. The above microorganism ATCC 55426 was deposited on May 12, 1993. The term "SC" denotes the designation given to the microorganism as part of the Squibb culture collection. Microorganisms of the genus Nocardioides were first disclosed for use in enzymatic syntheses in U.S. Pat. No. 5,516,676 which is incorporated by reference herein.

It should be understood that mutants of the biologically pure microorganisms *Nocardioides luteus* ATCC 55426 (SC 13912) are also contemplated by the present invention for use in the hydroxylation methods described herein, such as those modified by the use of chemical, physical (for example, x-rays) or biological means (for example, molecular biology techniques).

*Nocardioides luteus* ATTC 55426 (SC 13912) may be cultivated on a medium of 2% toasted nutrisoy, 0.5% glucose, 0.5% yeast extract, and 0.5% $K_2PO_4$ adjusted to pH 7 with $KH_2PO_4$. *Nocardioides luteus* ATTC 55426 (SC 13912) may also be cultivated on Medium A 94 (corn steep liquor (35 grams), Cerelose (20 grams), $(NH_4)_2SO_4$ Reagent Grade (5 grams), $CaCO_3$ (3.5 grams), soy bean oil (5 ml) and distilled water (1 liter)). This organism was isolated from soil (from a sample from New Brunswick, N.J.), and is a gram positive, non-motile organism, exhibiting aerobic growth on a variety of media. On solid YS medium (0.2% yeast extract, 1% starch), the mycelium is dark cream colored. Microscopically, growth in liquid culture is characterized by mycelial aggregates consisting of abundantly branching hyphae.

Exemplary enzymes for use in the present method are hydroxylases. Preferred enzymes include those derived from microorganisms, particularly those microorganisms described above. Enzymes may be isolated, for example, by extraction and purification methods, such as exchange chromatography, followed by hydrophobic interaction chromatography and gel filtration. The present invention further provides the enzymes capable of the present hydroxylation which may be isolated from *Nocardioides luteus* ATCC 55426 (SC 13912), for example by the above techniques.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic hydroxylation method of the present invention may be carried out subsequent to the fermentation of the microorganism (two-stage fermentation and hydroxylation), or concurrently therewith, that is, in the latter case, by in situ fermentation and hydroxylation (single-stage fermentation and hydroxylation).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources may include N—Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements may include magnesium, manganese, calcium, cobalt, nickel, iron, sodium and potassium salts.

Phosphates may also be added in trace or, preferably, greater than trace amounts.

The medium employed may include more than one carbon or nitrogen source or other nutrient.

Preferred media for growth include aqueous media, particularly those described in the Examples herein.

The agitation and aeration of the reaction mixture affects the amount of oxygen available during the hydroxylation process when conducted, for example, in shake-flask cultures or fermentor tanks during growth of microorganisms. The agitation range from 100 to 250 RPM is preferred; aeration of about 1 to 10 volumes of air per volume of media per minute is preferred.

For growth of the microorganisms and/or hydroxylation according to the method of the present invention, the pH of the medium is preferably from about 6 to about 8.5, and the temperature is preferably from about 24° C. to about 37° C. Hydroxylation may, for example, be carried out in vitro over time periods such as 1 to 50 hours, or preferably until the yield of desired product is maximized. It is preferred to conduct the hydroxylation of the present invention at a pH of from 6 to 8, particularly under non-basic conditions. The amount of enzyme or microorganism employed relative to the starting material is selected to allow catalysis of the enzymatic hydroxlyation of the present invention.

Separation

The 6-α-hydroxy-7-deoxytaxane products of the process of the present invention and coupled products such as those described below, may be isolated and purified, for example, by methods such as extraction, distillation, crystallization, and column chromatography. Extraction from the reaction with a resin such as XAD-7 (Rohm and Haas) is useful for the intitial isolation and purification.

Utility

Taxanes are diterpene compounds containing a taxane moiety as described above. Of particular interest are taxanes containing a taxane moiety in which the 11, 12-positions are bonded through an ethylenic linkage, and in which the 7-position is deoxygenated, which taxanes are exemplified by 7-deoxybaccatin III. Taxanes such as 7-deoxybaccatin III are essential precursors in the semisynthesis of paclitaxel analogs which may be used as antitumour agents to treat patients suffering from cancers, such as breast, ovarian, colon or lung cancers, melanoma and leukemia.

The 6-α-hydroxy-7-deoxytaxanes obtained by the hydroxylation method of the present invention are particularly useful as intermediates in the preparation of taxanes having a C-13 hydroxyl group which may be subsequently coupled with C-13 sidechain-forming compounds to obtain C-13 sidechain-bearing taxanes, particularly 6-α-hydroxy-7-deoxy paclitaxel.

Paclitaxel is converted to 6-α-hydroxy paclitaxel in human liver by cyp2CP, and loses most of its cytotoxicity in the process of this hydroxylation. To avoid this loss of cytotoxicity, second and third generation paclitaxel analogs are being developed. Paclitaxel analogs such as 6-α-hydroxy-7-deoxytaxanes or compounds thereof may be useful as second and third generation anticancer agents.

Preferred Compounds

It is preferred to employ taxanes of the formula II or salts thereof in the method of the present invention, whereby enzymatic hydroxylation provides the corresponding compounds of the formula I or salts thereof. In formula I and II, $R_1$ is preferably acetyl or hydroxy; $R_2$ is methyl; $R_3$ is phenyl; $R_4$ is hydrogen; $R_5$ is a hydrogen, alkyl, alkenyl, alkynyl, cycloalkyl, cycloalkenyl, aryl or heterocyclo; and $R_6$ is hydrogen, a hydroxyl protecting group such as triethylsilyl, or an acyl group such as a paclitaxel side chain.

Exemplary starting taxanes of the of the formula II are 7-deoxybaccatin III or 7-deoxy-10-deacetylbaccatin III. Preferred hydroxylation products are 6-α-hydroxy-7-deoxybaccatin III or 6-α-hydroxy-7-deoxy-10-deacetylbaccatin III.

Salts or solvates such as hydrates of the reactants or products may be employed or prepared as appropriate in any of the methods of the present invention.

The present invention is further described by the following examples which are illustrative only, and are in no way intended to limit the scope of the instant claims.

EXAMPLE 1

Identification of Hydroxylation Activity in *Nocardioides luteus* SC13912

The reaction of this Example proceeded as set forth in Scheme 1 following. Medium: 0.5% toasted nutrisoy, 2% glucose, 0.5% yeast extract, 0.5% $K_2HPO_4$, 0.5% NaCl, adjusted to pH 7 with HCl. 10 ml medium in a 50 ml flask was inoculated with 0.1 ml culture from a frozen vial of *Nocardioides luteus* SC 13912. After 1 day at 28° C., 200 rpm, 7-deoxybaccatin III (1 mg in 0.1 ml methanol) was added and the incubation was continued for 3 days. 10 ml of methanol was added to the flask and a sample was analyzed by HPLC. About 56% of the area counts from the substrate were converted to 7-deoxy-10-deacetylbaccatin III, 11% to a 10.0 min. peak and 38% to a 5.1 min. peak. The material was extracted with ethyl acetate, dried and purified by solid phase extraction. MS analysis showed a product with the same 5.1 min. HPLC retention time and $(M+NH_4)^+=562$ as 6-α-hydroxy-7-deoxy-10-deacetylbaccatin III.

HPLC method
Column: Hewlett Packard Hypersil 5 ODS C18 200×4.6 mm
mobile phase: 48% methanol, 52% water
flow rate: 1 ml/min
detection: 235 nm
Retention times of HPLC Markers are set forth in Table 1 as follows:

TABLE 1

| Compound | ret. time min |
|---|---|
| 7-deoxybaccatin III | 21.937 |
| 7-deoxy-10-deacetylbaccatin III | 12.217 |
| 6-α-hydroxy-7-deoxy-10-deacetyl baccatin III | 5.112 |
| 6-β-hydroxy-7-deoxy-10-deacetyl baccatin III | 4.793 |

Scheme 1

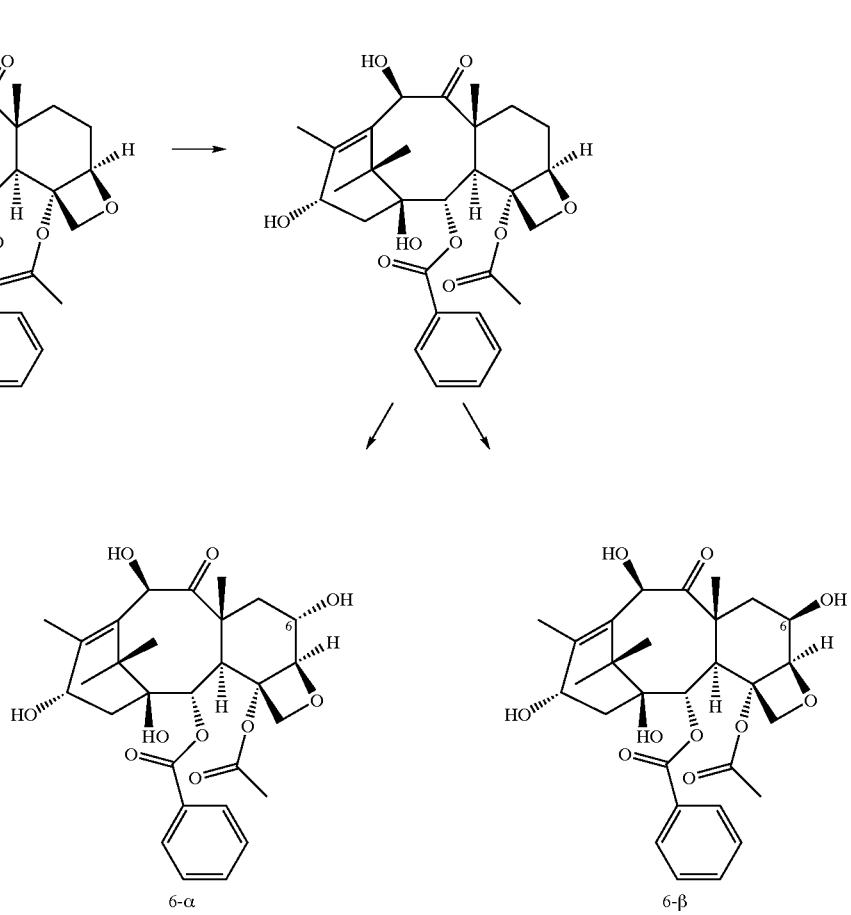

EXAMPLE 2

Hydroxylation by Washed Cells

A. Growth of cells

Medium: 2% toasted nutrisoy, 0.5% glucose, 0.5% yeast extract, 0.5% $K_2HPO_4$ adjusted to pH 7 with $KH_2PO_4$.

Inoculum: 1 vial *Nocardioides luteus* SC 13912 was added to 100 ml of the above-referenced medium in a 500 ml flask and incubated at 28° C., 200 rpm for 24 h. 10 ml of this culture was added to 500 ml of the above medium in a 2 L flask and incubated at 28° C. 200 rpm for 24 h. Fermentor: The 500 ml culture was used to inoculate 16 L of the above medium containing 8 ml of SAG antifoam in a Braun fermentor. Fermentation was at 28°, 500 rpm, 1 vvm air flow, 690 millibar gauge pressure for 30 h. Cell paste (1023 g) was recovered with a Cepa centrifuge, washed with 8 L 50 mM phosphate buffer pH 6 and stored at −70° C.

B. Biotransformation 100 g cell paste was dispersed in 1 L 0.1M potassium phosphate buffer pH 6 containing 0.4% glucose, using a Janke and Kunkel Ultraturrax T25 homogenizer. 50 ml aliquots of stirred cell suspension were pipetted into twenty 500 ml flasks. 7-deoxybaccatin III (5 mg in 0.5 ml methanol) was added to each flask and the flasks were shaken at 28° C., 200 rpm.) 0.5 ml samples were taken from one of the flasks and quenched with 0.5 ml methanol to monitor the reaction. After 18.5 h, 7-deoxybaccatin III was gone, 7-deoxy-10-deacetylbaccatin III was close to zero, and a new 5.1 min peak was present. The contents of the 20 flasks were pooled and extracted with 1 L ethyl acetate to stop the reaction. After extractive workup and flash chromatography, 60 mg of impure baccatin derivative was isolated which was identified by NMR as a 6-α-hydroxy-7-deoxy-10-deacetylbaccatin III (containing about 10% of the β-hydroxy isomer).

EXAMPLE 3

Hydroxylation of 7deoxy-10-deacetylbaccatin III

*N. luteus* cells were grown for 50 hours on a 500-liter scale in medium described in Example 2, using a 200 ml inoculum. Cell paste (28.0 kg) was recovered with a Sharples centrifuge, washed with 8 L 50 mM phosphate buffer pH 7 and stored at −70°.

0.5 g cells were dispersed in 5 ml 0.1 M potassium phosphate buffer pH 6.5 containing 2.5% glucose and 0.25 M NaCl using a T8 Ultraturrax (Janke & Kunkel GmBH & Co.). 1.0 mg 7-deoxy-10-deacetylbaccatin III in 0.1 ml methanol was added and the cell suspension was incubated on an Innova 4900 shaker (New Brunswick Scientific) at 28° C., 200 rpm. After 24 h, a sample of 0.5 ml was diluted with 0.5 ml methanol, vortexed and allowed to stand for at least 5 min before filtering into an HPLC vial. A 47.3% yield of 6-α-hydroxy-7-deoxy-10-deacetylbaccatin III was measured by HPLC. The concentration of 6-β-hydroxy-7-deoxy-10-deacetylbaccatin III was 16.3% of the α-isomer. HPLC:

column: HP hypersil 5 m ODS 200×4.6 mm
mobile phase: 40% methanol, 1 ml/min
temperature: 40° C.
detection: 235 nm
injection volume: 20 ml

| retention times: | 7-deoxy-10-deacetylbaccatin III | 27.6 min |
|---|---|---|
| | 6-α-hydroxy-7-deoxy-10-deacetylbaccatin III | 9.25 min |
| | 6-β-hydroxy-7-deoxy-10-deacetylbaccatin III | 8.35 min |

10-decetylbaccatin III was used as a standard for quantition of all compounds. It is assumed that the mM absorbances of all compounds are the same. The UV spectra are superimposable.

What is claimed is:

1. A compound of the formula:

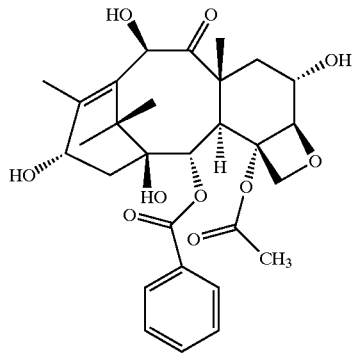

prepared by a method comprising the steps of contacting at least one 7-deoxytaxane with an enzyme or microorganism capable of catalyzing the hydroxylation of said 7-deoxytaxane at the 6-position, and effecting said hydroxylation.

2. A compound of the formula:

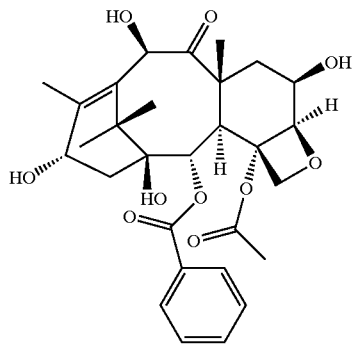

prepared by a method comprising the steps of contacting at least one 7-deoxytaxane with an enzyme or microorganism capable of catalyzing the hydroxylation of said 7-deoxytaxane at the 6-position, and effecting said hydroxylation.

3. A compound of the formula:

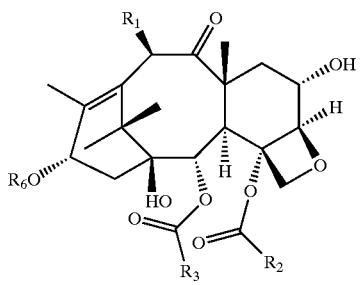

wherein

R$_1$ is hydrogen, hydroxyl, R$_4$—O—, or R$_5$—C(O)—O—;

R$_2$ and R$_3$ are independently hydrogen, alkyl, alkenyl, alkynyl, cycloalkyl, cycloalkenyl, aryl, or heterocyclo;

R$_4$ is a hydroxyl protecting group;

R$_5$ is hydrogen, alkyl, alkenyl, alkynyl, cycloalkyl, cycloalkenyl, aryl, or heterocyclo; and R$_6$ is hydrogen, a hydroxyl protecting group, or an acyl group; or a salt thereof.

4. A compound of claim 3 wherein R$_6$ is triethylsilyl, a paclitaxel sidechain, a cephalomannine sidechain, or a taxol analog sidechain.

5. A compound of claim 3 of the formula

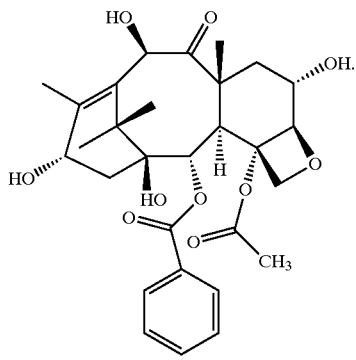

6. A compound of the formula:

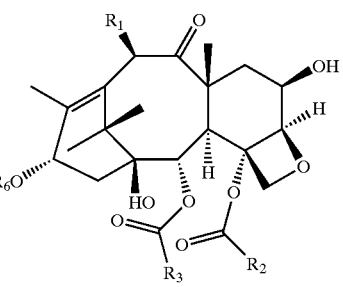

wherein

R$_1$ is hydrogen, hydroxyl, R$_4$—O—, or R$_5$—C(O)—O—;

R$_2$ and R$_3$ are independently hydrogen, alkyl, alkenyl, alkynyl, cycloalkyl, cycloalkenyl, aryl, or heterocyclo;

R$_4$ is a hydroxyl protecting group;

R$_5$ is hydrogen, alkyl, alkenyl, alkynyl, cycloalkyl, cycloalkenyl, aryl, or heterocyclo; and R$_6$ is hydrogen, a hydroxyl protecting group, or an acyl group; or a salt thereof.

7. A compound of claim 6 wherein R$_6$ is triethylsilyl, a paclitaxel sidechain, a cephalomannine sidechain, or a taxol analog sidechain.

8. A compound of claim 6 of the formula

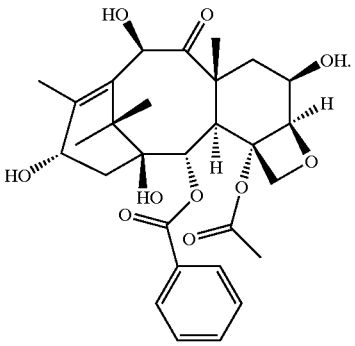

* * * * *